US012678482B2

(12) United States Patent
Barton et al.

(10) Patent No.: US 12,678,482 B2
(45) Date of Patent: Jul. 14, 2026

(54) METHODS AND COMPOSITIONS FOR TREATING CHRONIC LUNG DISEASES

(71) Applicant: Oak Hill Bio Limited, Cheshire (GB)

(72) Inventors: Norman Barton, Lexington, MA (US); Alexandra Mangili, Lexington, MA (US)

(73) Assignee: OAK HILL BIO LIMITED, Cheshire (GB)

( * ) Notice: Subject to any disclaimer, the term of this patent is extended or adjusted under 35 U.S.C. 154(b) by 955 days.

(21) Appl. No.: 17/317,152

(22) Filed: May 11, 2021

(65) Prior Publication Data

US 2022/0088132 A1     Mar. 24, 2022

Related U.S. Application Data

(63) Continuation of application No. 16/127,988, filed on Sep. 11, 2018, now abandoned.

(60) Provisional application No. 62/557,113, filed on Sep. 11, 2017.

(51) Int. Cl.
| | |
|---|---|
| *A61K 38/17* | (2006.01) |
| *A61K 9/00* | (2006.01) |
| *A61K 38/30* | (2006.01) |
| *A61P 11/00* | (2006.01) |
| *A61P 25/00* | (2006.01) |
| *A61P 27/00* | (2006.01) |

(52) U.S. Cl.
CPC .......... *A61K 38/1754* (2013.01); *A61K 38/30* (2013.01); *A61P 11/00* (2018.01); *A61P 25/00* (2018.01); *A61P 27/00* (2018.01); *A61K 9/0019* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 5,783,556 A | 7/1998 | Clark et al. | |
| 6,071,880 A | 6/2000 | Acott et al. | |
| 6,436,897 B2 | 8/2002 | Danko et al. | |
| 7,144,707 B2 * | 12/2006 | Smith | A61P 1/04 |
| | | | 435/7.1 |
| 7,354,994 B2 | 4/2008 | Summer et al. | |
| 7,776,820 B2 | 8/2010 | Smith et al. | |
| 7,968,679 B2 | 6/2011 | Sleevi et al. | |
| 8,518,877 B2 | 8/2013 | Hellstrom et al. | |
| 9,168,289 B2 | 10/2015 | Laron | |
| 9,463,222 B2 | 10/2016 | Hellstrom et al. | |
| 9,517,266 B2 | 12/2016 | Lim et al. | |
| 2002/0028764 A1 | 3/2002 | Grofte et al. | |
| 2004/0053838 A1 * | 3/2004 | Smith | A61P 5/00 |
| | | | 435/7.1 |
| 2010/0204101 A1 * | 8/2010 | Hellstrom | A61P 9/10 |
| | | | 514/1.1 |
| 2012/0270782 A1 | 10/2012 | Gopinath et al. | |
| 2014/0199286 A1 | 7/2014 | Zhao et al. | |
| 2019/0151411 A1 | 5/2019 | Barton et al. | |

FOREIGN PATENT DOCUMENTS

| | | |
|---|---|---|
| CN | 101969983 A | 2/2011 |
| EP | 1082133 B1 | 7/2004 |
| EP | 1646650 B1 | 4/2009 |
| EP | 1828225 B1 | 3/2010 |
| EP | 1402266 B1 | 1/2011 |
| EP | 2148695 B1 | 10/2014 |
| WO | WO 1999/062536 A2 | 12/1999 |
| WO | WO 2002/043578 A2 | 6/2002 |
| WO | WO 2006/069029 A1 | 6/2006 |
| WO | WO 2008/130315 A1 | 10/2008 |

OTHER PUBLICATIONS

Drugs R D. 2005;6(2):120-7, Abstract provided (Year: 2005).*
Shire Jun. 30, 2016 Phase 2 Trial Press Release for SHP607 in Extremely Premature Infants, 5 pages, Jun. 30, 2016 (Year: 2016).*
ACROBiosystems webpage for IGF-1 R Protein, 3 pages, downloaded Apr. 20, 2020 (Year: 2020).*
Pharmacodia description of Mecasermin Rinfabate, last updated Oct. 28, 2015 (Year: 2015).*
Drugs R D. 2005;6(2):120-127 (Year: 2005).*
Hellstrom, Current Pharmaceutical Design, 2017, 23, 5964-5970 (Year: 2017).*
Katzung, p. 37, Basic & Clinical Pharmacology, 14th Ed. 2018, Chapters 2 and 3 provided (Year: 2018).*
Screen shot of www.clinicaltrials.gov, downloaded from the internet Feb. 27, 2024, 1 page (Year: 2024).*
Ley et al., Pediatric Research, vol. 73, pp. 68-74 (Year: 2013).*
Hansen-Pupp et al., "Continuous Longitudinal Infusion of rhIGF-1/rhIGFBP-3 in Extremely Preterm Infants: Evaluation of Feasibility in a Phase II Study", Growth Hormone & IGF Research, Aug. 31, 2017, pp. 44-51.
www.pipelinerreview.com, "Shire Announces Top-Line Results for Phase 2 Trial of SHP607 in Extremely Premature Infants", https://pipelinereview.com/Index.php/20160630617581/Proteins-and-Peptides/Shire-Announces-Top-Line-Results-for-Phase-2-Trial-of-SHP607-in-Extremely-Premature-Infants.html, Jun. 30, 2016, pp. 1-2.
U.S. National Library of Medicine—ClinicalTrials.gov "A Clinical Efficacy and Safety Study of SHP607 in Preventing Chronic Lung Disease in Extremely Premature Infants," Apr. 17, 2017, 9 pages.
ACROBiosystems webpage for IGF-1 R Protein, 3 pages, downloaded Apr. 20, 2020.
Chung et al., "Development and verification of a pharmacokinetic model to optimize physiologic replacement of rhIGF-1/rhIGFBP-3 in preterm infants", Pediatric Research, vol. 81, No. 3, Mar. 1, 2017, pp. 504-510.

(Continued)

*Primary Examiner* — Joseph Fischer

(74) *Attorney, Agent, or Firm* — Debora Plehn-Dujowich; Eckert Seamans Cherin & Mellott, LLC

(57)     ABSTRACT

The present invention provides, among other things, methods and compositions for treating Chronic Lung Disease (CLD), comprising administering to a subject in need of treatment a composition comprising insulin-like growth factor-1 (IGF-1) or an agonist or an analog thereof.

6 Claims, No Drawings

(56)                    References Cited

OTHER PUBLICATIONS

Guideline for Industry Dose-Response Information to Support Drug Registration, ICH-4, 1994.

Hack et al., "Long-term developmental outcomes of low birth weight infants", The Future of Children, vol. 5, 1995, pp. 176-196.

Hellstrom et al., "IGF-1 in the clinics: Use in retinopathy of prematurity", Growth Hormone and IGF Research, vol. 30, Sep. 28, 2016, pp. 75-80.

Hellstrom et al., "IGF-1 as a drug for preterm infants: A step-wise clinical development", Current Pharmaceutical Design, vol. 23, No. 38, 2017, pp. 5964-5970.

International Search Report and Written Opinion for PCT/US18/50427, dated Dec. 17, 2018.

International Preliminary Report on Patentability for PCT/US18/50427, dated Mar. 26, 2020.

Ley et al., "Longitudinal infusion of a complex of insulin-like growth factor-I and IGF-binding protein-3 in five preterm infants: pharmacokinetics and short-term safety", Pediatric Research, vol. 73, No. 1, 2013, pp. 68-74.

Liegl et al., "IGF-1 in retinopathy of prematurity, a CNS neurovascular disease", Early Human Development, Shannon, IR, vol. 102, Sep. 17, 2016, pp. 13-19.

Pharmacodia description of Mecasermin Rinfabate, last updated Oct. 28, 2015.

Shire Jun. 30, 2016 Phase 2 Trial Press Release for SHP607 in Extremely Premature Infants, 5 pages, Jun. 30, 2016.

Albertine etal., "Pilot Dose-Ranging of rhIGF-1/rhIGFBP-3 in a Preterm Lamb Model of Evolving Bronchopulmonary Dysplasia", Pediatric Research, vol. 93(6): 25 pages, May 2023.

Boisclair et al., "The Acid-Labile Subunit (ALS) of the 150 KDA IGF-Binding Protein Complex: An Important but Forgotten Component of the Circulating IGF System", Journal of Endocrinology, vol. 170: pp. 63-70, 2001.

Christiansen et al., "Insulin-Like Growth Factor-1 Supplementation Promotes Brain Maturation in Preterm Pigs", Eneuro, vol. 10(4): 1-15, Apr. 2023.

Costa et al., "Anatomy and Physiology of the Enteric Nervous System", Gut, supplementary IV, pp. iv15-iv19, 2000.

Dani et al., "Recombinant Human (rh)IGF-1/rhIGFBP-3 for Prevention of Bronchopulmonary Dysplasia", European Respiratory Journal, vol. 50(OA3423): 6 pages, 2017.

Dempsey, Eugene M. "Challenges in Treating Low Blood Pressure in Preterm Infants", Children, vol. 2: 272-288, Jun. 15, 2015.

Holgersen et al., "Clinical Outcome and Gut Development after Insulin-Like Growth Factor-1 Supplementation to Preterm Pigs", Frontiers in Pediatrics, pp. 1-17, Aug. 5, 2022.

Hu et al., "Paracrine IGF-1 Activates SOD2 Expression and Regulates ROS/p53 Axis in the Treatment of Cardiac Damage in D-Galactose-Induced Aging Rats after Receiving Mesenchymal Stem Cells", Journal of Clinical Medicine, vol. 11(4419): 1-15, Jul. 29, 2022.

Ley et al., "rhIGF-1/rhIGFBP-3 in Preterm Infants: A Phase 2 Randomized Controlled Trial", The Journal of Pediatrics, vol. 206: pp. 56-65, Mar. 2019.

Madathil et al., "Chapter 7: IGF-1/IGF-R Signaling in Traumatic Brain Injury, Impact on Cell Survival, Neurogenesis, and Behavioral Outcome", Brain Neurotrauma: Molecular, Neuropsychological, and Rehabilitation Aspects, CRC Press/Taylor & Francis, 24 pages, 2015.

Scientific Discussion, EMEA, pp. 1-39, 2007.

Xu et al., "Effect of IGF-1C Domain-Modified Nanoparticles on Renal Ischemia—Reperfusion Injury in Mice", Renal Failure, vol. 44(1): 1377-1388, Jul. 1, 2022.

Yan et al., "Macrophage-Derived IGF-1 Protects the Neonatal Intestine against Necrotizing Enterocolitis by Promoting Microvascular Development", Communications Biology, vol. 5(320): 1-13, Apr. 6, 2022.

Zhong et al., "Insulin-Like Growth Factot-1 Supplementation Promotes Kidney Development and Alleviate Renal Inflammation in Preterm Pigs", BioRxiv, 31 pages, Jun. 5, 2023.

"IGF-I R Public Drug Information" ACROBiosystems Webpage for IGF-1R Protein, online available at <www.acrobiosystems.com/L-284-IGF-1%20R.html>, downloaded Apr. 20, 2020, 4 pages.

General Guidelines for Clinical Evaluation of New Pharmaceutical Products, Jun. 29, 1992, Yakushin Yakuhin No. 43, Notice of the Director of the New Pharmaceutical Products Division, pharmaceutical practice bureau, Ministry of Health and Welfare.

Turner et al., Arch Dis Child 2017, "Evaluation of RHIGF—1/RHIGFBP—3 to Establish and Maintain Physiological Intrauterine Serum IGF—1 Levels Early After Birth in Extremely Preterm Infants", European Society for Developmental Perinatal and Paediatric Pharmacology Congress, Leuven, Jun. 21-23, 2017, pp. 42, [URL] https://www.esdppp.org/app/download/10920635152/Archdischild-2017 - esdppp.pdf?t=1575614335.

Sharma, J. et al, Pharmacokinet Pharmacodyn (2014) 41:S12, M—013.

Anonymous, Jul. 3, 2019, retrieved from https://onderzoekmetmensen.nl/en/node/52648/pdf—A phase 2b, multicenter, randomized, open-label, two-arm study to evaluate the clinical efficacy and safety of OHB-607 compared to standard neonatal care for the prevention of bronchopulmonary dysplasia, the most common cause of chronic lung disease of prematurity.

* cited by examiner

METHODS AND COMPOSITIONS FOR TREATING CHRONIC LUNG DISEASES

CROSS-REFERENCE TO RELATED APPLICATIONS

This application is a continuation application of application Ser. No. 16/127,988, filed on Sep. 11, 2018, which claims priority to U.S. Provisional Application Ser. No. 62/557,113 filed Sep. 11, 2017, the disclosure of which is hereby incorporated by reference in its entirety.

BACKGROUND

Of an estimated 4.2 million live births in the United States each year, approximately 383,000 (about 9%) occur prematurely. Preterm labor and its complications are major perinatal public health issues in developed societies today. Low birth-weight infants or infants born prematurely miss a major part of the critical period of in utero growth. They account for half of all infant deaths and three-quarters of long-term morbidity. They impose a heavy burden on the national economy, because of the high costs of special care in both the neonatal period and over the life-span of survivors. Many survivors also have diminished quality of life because of physical damage resulting directly from prematurity.

The length of a normal pregnancy or gestation is considered to be 40 weeks (280 days) from the date of conception. Infants born before 37 weeks gestation are considered premature and may be at risk for complications. Advances in medical technology have made it possible for infants born as young as 23 weeks gestational age (17 weeks premature) to survive. Infants born prematurely are at higher risk for death or serious complications due to their low birth weight and the immaturity of their body systems. Low birthweight, defined by a cut-off of 2,500 g, serves as a marker for high risk newborns, as it is correlated with prenatal risk factors, intrapartum complications and neonatal disease, and is composed largely of preterm births. Studies on very low birth-weight, defined as less than 1,500 g or less than 1,000 g cut-offs that identify infants at highest risk, those with high rates of severe respiratory and neurological complications associated with extreme prematurity. (See. Hack. M., Klein, N. K., & Taylor, H. G., Long-term developmental outcomes of low birth weight infants. The Future of Children, 5,176-196 (1995)).

The lungs, digestive system, and nervous system (including the brain) are not fully developed in premature babies, and are particularly vulnerable to complications. The most prevalent medical problems encountered in preterm infants are retinopathy of prematurity, developmental delay, mental retardation, bronchopulmonary dysplasia (BPD), necrotizing enterocolitis, and intraventricular hemorrhage.

Chronic Lung Disease (CLD) is a particularly complicated and life threatening condition in premature infants. Premature infants, especially those extremely premature infants, are at very high risk for developing chronic lung disease, with bronchopulmonary dysplasia (BPD) at term being an early manifestation. The long term trajectory of pulmonary outcomes in infants born extremely premature commonly starts with antenatal risk factors, followed by respiratory distress syndrome (RDS) in the first hours or days of life requiring respiratory support, leading up to a diagnosis of BPD in those who survive to term equivalence, and finally chronic respiratory morbidity as they grow into infancy, early childhood and often even school age or adolescence that results in more frequent re-hospitalizations and ER visits for respiratory causes, the need for respiratory medications or home respiratory support, and many suffer from a form of reactive airway disease that continues to limit their quality of life. A large proportion of infants with BPD at 36 weeks will develop persistent lung disease at 12-24 months corrected age, but there are also infants without a diagnosis of BPD who develop Chronic Lung Disease later in infancy.

SUMMARY

The present invention provides an effective treatment of Chronic Lung Disease (CLD) in premature infants. The invention is, in part, based on the insights that a combination of IGF-1 and insulin-like growth factor binding protein-3 (IGFBP-3) can improve not only the short term outcomes but also the longer term conditions related to chronic lung disease, resulting in significantly improved growth and development arch of infants born extremely premature starting immediately after birth when cut off from the maternal supply of IGF-1 and through its replacement.

In one aspect of the present disclosure, a method of treating Chronic Lung Disease (CLD) is provided, comprising administering to a subject in need of treatment, a composition comprising insulin-like growth factor-1 (IGF-1) or an agonist or an analog thereof. In some embodiments, a method of treating CLD is provided, comprising administering to a subject in need of the treatment, a composition comprising the IGF-I or agonist or analog thereof comprising IGF-1 and an IGF binding protein. In some embodiments, the composition comprises the IGF-I or agonist or analog thereof and also comprises IGF-1 and insulin-like growth factor binding protein-3 (IGFBP-3).

In some embodiments, the subject in need of the treatment is an infant. In some embodiments, the subject is a premature infant, wherein the infant is prematurely born by at least 1 week, 2 weeks, 3 weeks, 4 weeks, 5 weeks, 6 weeks, 7 weeks, 2 months, 10 weeks or 3 months.

In some embodiments, the subject in need of the treatment is administered a composition comprising the IGF-I or agonist or analog, wherein the composition is administered subcutaneously, intravenously, intramuscularly, or orally. In some embodiments, the IGF-I or agonist or analog thereof is administered intravenously. In some embodiments, the IGF-I or agonist or analog thereof is administered at a dosage of about 100 to 500 micrograms/kg/24 hours. In some embodiments, the IGF-I or agonist or analog thereof is administered at a dosage of between 100 micrograms/kg/24 hours and 450 micrograms/kg/24 hours. In some embodiments, the IGF-I or agonist or analog thereof is administered at a dosage of between 150 micrograms/kg/24 hours and 400 micrograms/kg/24 hours. In some embodiments, the IGF-I or agonist or analog thereof is administered at a dosage of between 200 micrograms/kg/24 hours and 400 micrograms/kg/24 hours. In some embodiments, the IGF-I or agonist or analog thereof is administered at a dosage of between 250 micrograms/kg/24 hours and 400 micrograms/kg/24 hours. In some embodiments, the IGF-I or agonist or analog thereof is administered at a dosage of about 250 micrograms/kg/24 hours. In some embodiments, the IGF-I or agonist or analog thereof is administered at a dosage of about 400 micrograms/kg/24 hours. In some embodiments, the IGF-I or agonist or analog thereof is administered from the time of birth up to post-menstrual age (PMA) of about 24-34 weeks. PMA is defined as the age in weeks of an infant in weeks when he or she is discharged from hospital, or the age of death, or first birthday, whichever comes first. It is calculated as the sum of (i) the product of total gestation weeks and seven, (ii) the number of gestation days, and (iii) the days of length of stay in the hospital after birth. In some embodiments, the IGF-I or agonist or analog thereof is administered from the time of birth up to PMA of about 28 to 32 weeks. In some embodiments, the IGF-I or agonist or analog thereof is administered from the time of birth up to PMA of about 29 weeks plus 6 days.

In some embodiments of the disclosure, the subject has reduced IGF-1 serum levels. In some embodiments, the reduced IGF-1 serum levels are below 60 micrograms/L. In some embodiments, the reduced IGF-1 serum levels are below 50 micrograms/L. In some embodiments, the reduced IGF-1 serum levels are below 40 micrograms/L. In some embodiments, the reduced IGF-1 serum levels are about 30 to 50 micrograms/L.

In some embodiments, the IGF-1 is recombinantly produced. In some embodiments, the IGFBP-3 is recombinantly produced. In some embodiments, the IGF-1 and the IGFBP-3 are complexed prior to administration to the subject. In some embodiments, the IGF-1 and IGFBP-3 are complexed in equimolar amounts.

The method provided herein comprises embodiments where the administration of the IGF-I or agonist or analog results in reduced incidence of Chronic Respiratory Morbidity (CRM) through 12 months corrected age (CA). The corrected age of an infant is the adjusted age of the infant based on his or her due date. Taking the term of the pregnancy to be 40 weeks (i.e., due date), a prematurely born infant gets a corrected age where the excess time it has existed outside the mother's body is subtracted from its real age. In some embodiments, the administration of the IGF-I or agonist or analog results in reduced incidence of Bronchopulmonary Dysplasia (BPD) through postmenstrual age (PMA) 24 weeks to 12 months. For example, the administration of the IGF-I or agonist or analog results in reduced incidence of BPD through PMA 24 weeks, 28 weeks, 30 weeks, 32 weeks, 34 weeks, 36 weeks, or 38, or 40 weeks, 45 weeks, 50 weeks, or 52 weeks. In some other embodiments, the administration of the IGF-I or agonist or analog results in reduced incidence of BPD through PMA 6 months, 8 months, 10 months, or 12 months. In some embodiments, the administration of the IGF-I or agonist or analog thereof results in reduced incidence of Severe Intraventricular Hemorrhage (IVH) Grade III or IV through postmenstrual age (PMA) 24 weeks, 30 weeks, 36 weeks, 40 weeks, 6 months, 8 months, 10 months, or 12 months. In some embodiments, the administration of the IGF-I or agonist or analog thereof results in reduced incidence of retinopathy of prematurity (ROP) through postmenstrual age (PMA) 24 weeks, 30 weeks, 36 weeks, 40 weeks, 6 months, 8 months, 10 months, or 12 months.

The method disclosed herein comprises embodiments where the administration of the IGF-I or agonist or analog results in increased Functional Status as Assessed by PREMature Infant Index (PREMII) through postmenstrual age (PMA) 24 weeks, 30 weeks, 32 weeks, 34 weeks, 36 weeks, 38 weeks, 40 weeks, 50 weeks, 6 months, 8 months, 10 months, or 12 months.

It is to be understood that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains.

DETAILED DESCRIPTION

The present invention provides methods and compositions for treating Chronic Lung Disease. The compositions and methods provided herein are particularly effective in treating Chronic Lung Disease in premature infants, especially those extremely premature infants. In some embodiments, a method of the invention involves administering to a subject in need of treatment (e.g., a premature infant) insulin-like growth factor-1 (IGF-1) or an agonist or an analog thereof. In some embodiments, the IGF-I or agonist or analog thereof contains IGF-1 and an IGF binding protein (e.g., insulin-like growth factor binding protein-3 (IGFBP-3)).

Various aspects of the invention are described in detail in the following sections. The use of sections is not meant to limit the invention. Each section can apply to any aspect of the invention. In this application, the use of "or" means "and/or" unless stated otherwise.

Definitions

"Preterm" or "preterm birth" or "prematurity" or "premature infant" or "premature baby", or grammatical equivalents, refers to birth of a patient prior to 40 weeks of gestation or weighing 10% less than the average for the patient's gestational age. In some embodiments, a premature infant refers to an infant that was prematurely born by at least 1 week, 2 weeks, 3 weeks, 4 weeks, 1 month, 2 months, or 3 months.

"IGF-I" refers to insulin-like growth factor I from any species, including bovine, ovine, porcine, equine, and human, preferably human, and, if referring to exogenous administration, from any source, whether natural, synthetic, or recombinant, provided that it will bind IGF binding protein at the appropriate site. IGF-I can be produced recombinantly, for example, as described in PCT publication WO 95/04076.

An "IGFBP" or an "IGF binding protein" refers to a protein or polypeptide from the insulin-like growth factor binding protein family and normally associated with or bound or complexed to IGF-I whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., Proc. Natl. Acad. Sci. USA, 92: 4472-4476 (1995) and Oh et al., J. Biol. Chem., 271: 30322-30325 (1996). PSF is described in Yamauchi et al., Biochemical Journal, 303: 591-598 (1994). ESM-1 is described in Lassalle et al., J. Biol. Chem., 271: 20458-20464 (1996). For other identified IGFBPs, see, e.g., EP 375.438 published Jun. 27, 1990; EP 369,943 published May 23, 1990; WO 89/09268 published Oct. 5, 1989; Wood et al., Molecular Endocrinology, 2: 1176-1185 (1988); Brinkman et al., The EMBO J., 7: 2417-2423 (1988); Lee et al., Mol. Endocrinol., 2: 404-411 (1988); Brewer et al., BBRC, 152: 1289-1297 (1988); EP 294.021 published Dec. 7, 1988; Baxter et al., BBRC, 147: 408-415 (1987); Leung et al., Nature, 330: 537-543 (1987); Martin et al., J. Biol. Chem., 261: 8754-8760 (1986); Baxter et al., Comp.

Biochem. Physiol., 91B: 229-235 (1988); WO 89/08667 published Sep. 21, 1989; WO 89/09792 published Oct. 19, 1989; and Binkert et al., EMBO J., 8: 2497-2502 (1989).

"IGFBP-3" refers to insulin-like growth factor binding protein 3. IGFBP-3 is a member of the insulin-like growth factor binding protein family. IGFBP-3 may be from any species, including bovine, ovine, porcine and human, in native-sequence or variant form, including but not limited to naturally-occurring allelic variants. IGFBP-3 may be from any source, whether natural, synthetic or recombinant, provided that it will bind IGF-I at the appropriate sites. IGFBP-3 can be produced recombinantly, as described in PCT publication WO 95/04076.

A "therapeutic composition." as used herein, is defined as comprising IGF-I, an analog thereof, or IGF-I in combination with its binding protein, IGFBP-3 (IGF-I/IGFBP-3 complex). The therapeutic composition may also contain other substances such as water, minerals, carriers such as proteins, and other excipients known to one skilled in the art.

"Analogs" of IGF-I are compounds having the same therapeutic effect as IGF-I in humans or animals. These can be naturally occurring analogs of IGF-I (e.g., truncated IGF-I) or any of the known synthetic analogs of IGF-I. See, for example, U.S. Pat. No. 5,473,054 for analog compounds of IGF-I.

"Agonists" of IGF-I are compounds, including peptides, which are capable of increasing serum and tissue levels of IGF, especially IGF-I, in a mammal and particularly in a human. See, for example, U.S. Pat. No. 6,251,865 for IGF agonist molecules.

"Developmental delay" as used herein shall mean abnormal neurogenesis which has the potential of leading to slowed mental progression in achieving developmental milestones. Developmental delay can, in some cases, be determined by means of electroencephalogram.

"Subject" as used herein means any mammal, including humans. In certain embodiments of the present invention the subject is an adult, an adolescent or an infant. Also contemplated by the present invention are the administration of the pharmaceutical compositions and/or performance of the methods of treatment in-utero.

As used herein, the term "treatment" (also "treat" or "treating") refers to any administration of a therapeutic composition (e.g., IGF-1 or an agonist or an analog thereof) that partially or completely alleviates, ameliorates, relieves, inhibits, delays onset of, prevents, reduces severity of and/or reduces incidence of one or more symptoms or features of a particular disease, disorder, and/or condition (e.g., Chronic lung disease). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein, or historical reference or data. A "control individual" is an individual afflicted with the same form of Chronic Lung Disease as the individual being treated, who is about the same age as the individual being treated (to ensure that the stages of the disease in the treated individual and the control individual(s) are comparable).

Chronic Lung Disease

The present invention may be used to treat any type of Chronic Lung Disease (CLD) including CLD that occurs in the adult especially the elderly and infants especially those premature or extremely premature infants. CLD involves a spectrum of diseases and disorders, including but not limited to COPD (emphysema and chronic bronchitis), asthma, cystic fibrosis, restrictive lung disease, and persistent infections.

Chronic Lung Disease of Prematurity

Extremely premature infants are at very high risk for developing chronic lung disease. Premature babies may need a breathing machine (ventilator) and extra oxygen to breathe. Chronic Lung Disease happens when a breathing machine or oxygen injures a premature baby's lungs. With a lung injury, the tissues inside a baby's lungs get inflamed. The tissue can break down, causing scarring. The scarring can cause trouble breathing, and the baby may need more oxygen. Lung injury may be caused by:

Prematurity: A premature baby's lungs aren't fully formed. This is especially true of the air sacs.

Low amounts of surfactant: This is a substance in the lungs that helps keep the tiny air sacs open.

Oxygen use: High amounts of oxygen can harm the cells in the lungs.

Breathing machine (mechanical ventilation): Air pressure can harm the lungs. This pressure may come from breathing machines, suctioning of the airways, and use of an endotracheal (ET) tube. An ET tube is a tube placed in your baby's windpipe (trachea) and connected to a breathing machine.

The long term trajectory of pulmonary outcomes in infants born extremely premature commonly starts with antenatal risk factors, followed by respiratory distress syndrome (RDS) in the first hours or days of life requiring respiratory support, leading up to a diagnosis of BPD in those who survive to term equivalence, and finally chronic respiratory morbidity as they grow into infancy, early childhood and often even school age or adolescence that results in more frequent re-hospitalizations and ER visits for respiratory causes, the need for respiratory medication or home respiratory support, and many suffer from a form of reactive airway disease that continues to limit their quality of life.

IGF-1 or an Agonist or an Analog Thereof

IGF-1 or an agonist or an analog thereof may be used to practice the present invention. IGF-I is a well-known regulator of postnatal growth and metabolism. See, Baker J, Liu J P. Robertson E J, Efstratiadis A. It has a molecular weight of approximately 7.5 kilodaltons (Kd). Most circulating IGF is bound to the IGF-binding protein, and more particularly to the IGFBP-3. IGF-I may be measured in blood serum to diagnose abnormal growth-related conditions.

Typically, a therapeutic composition suitable for treatment of CLD according to the present invention contains an IGF-1 and an IGF-1 binding protein such as IGF binding-proteins (IGFBPs). At least six distinct IGF binding-proteins (IGFBPs) have been identified in various tissues and body fluids. In some embodiments, a suitable therapeutic composition according to the present invention contains IGF-1 and IGFBP-3. IGF-1 and IGFBP-3 may be used as a protein complex or separately.

IGF-I and IGF-I binding proteins such as IGFBP-3 may be purified from natural sources or produced by recombinant means. For instance, purification of IGF-I from human serum is well known in the art (Rinderknecht et al. (1976) Proc. Natl. Acad. Sci. USA 73:2365-2369). Production of IGF-I by recombinant processes is shown in EP 0128733, published in December of 1984. IGFBP-3 may be purified from natural sources using a process such as that shown by Baxter et al. (1986, Biochem. Biophys. Res. Comm, 139: 1256-1261). Alternatively. IGFBP-3 may be synthesized recombinantly as discussed by Sommer et al., pp. 715-728, Modern Concepts Of Insulin-Like Growth Factors (E. M. Spencer, ed., Elsevier, N.Y., 1991). Recombinant IGFBP-3 binds IGF-I in a 1:1 molar ratio.

Pharmaceutical Composition and Therapeutic Use

The present invention provides compositions and methods for treating a patient suffering from a Chronic Lung Disease (CLD), in particular, CLD associated with prematurity. For example, the present invention may be used to treat a premature infant who is suffering from CLD or complication associated with CLD. In some embodiments, the present invention may be used to treat infant who is prematurely born by at least 1 week, 2 weeks, 3 weeks, 4 weeks, 1 month, 2 months, or 3 months. In some embodiments, the present invention may be used to treat extremely premature infant.

In one embodiment of the invention. IGF-I or an analog thereof is administered in combination with IGF binding protein capable of binding IGF-I. In some embodiment, the IGF binding protein capable of binding IGF-I is IGF binding protein 3 (IGFBP-3).

A composition comprising equimolar amounts of IGF-I and IGF-binding protein may be used. In some embodiments, the IGF-I and IGF binding protein are complexed prior to administration. The complex may be formed by mixing approximately equimolar amounts of IGF-I and IGF binding protein dissolved in physiologically compatible carriers such as normal saline, or phosphate buffered saline solution. In some embodiments, a concentrated solution of recombinant human IGF-I and a concentrated solution of recombinant human IGF binding protein are mixed together for a sufficient time to form an equimolar complex. In some embodiments, recombinant human IGF-I and recombinant human IGF binding protein are combined to form a complex during purification as described in International Patent Application No. WO 96/40736.

For therapeutic applications, IGF-I or an analog thereof may be suitably administered to a patient, alone or as part of a pharmaceutical composition, comprising the IGF-I or an analog thereof together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, nasal, topical (including buccal and sublingual), or parenteral (including subcutaneous, intramuscular, intravenous and intradermal) administration. The formulations may conveniently be presented in unit dosage form, e.g., tablets and sustained release capsules, and in liposomes, and may be prepared by any methods well known in the art of pharmacy. See, for example. Remington's Pharmaceutical Sciences. Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

The inventive methods disclosed herein provide for the parenteral an oral administration of IGF-I, an analog or an agonist thereof, or IGF-I or an analog in combination with IGF binding protein complex to infants in need of such treatment. Parenteral administration includes, but is not limited to, intravenous (IV), intramuscular (IM), subcutaneous (SC), intraperitoneal (IP), intranasal, and inhalant routes. In the method of the present invention, IGF-I, an agonist or an analog thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the patient. In some embodiments, the IGF-I or agonist or analog thereof is administered intravenously.

A pharmaceutical composition according to the present invention may be administered at various doses. For example, a suitable dosage may range from about 100 to 500 micrograms/kg/24 hours. In some embodiments, a suitable dosage may be or greater than about 100 micrograms/kg/24 hours, 150 micrograms/kg/24 hours, 200 micrograms/kg/24 hours, 250 micrograms/kg/24 hours, 300 micrograms/kg/24 hours, 350 micrograms/kg/24 hours, 400 micrograms/kg/24 hours, 450 micrograms/kg/24 hours, or 500 micrograms/kg/24 hours. In some embodiments, a pharmaceutical composition according to the invention is administered from the time of birth up to post-menstrual age (PMA) of about 24-34 weeks, up to PMA of about 28 to 32 weeks, up to PMA of about 29 weeks plus 6 days.

The method provided herein comprises embodiments where the administration of the IGF-I or agonist or analog results in reduced incidence of Chronic Respiratory Morbidity (CRM) through 12 months corrected age (CA). In some embodiments, the administration of the IGF-I or agonist or analog results in reduced incidence of Bronchopulmonary dysplasia (BPD) through postmenstrual age (PMA) 36 weeks, 40 weeks, 6 months, 8 months, 10 months, or 12 months. In some embodiments, the administration of the IGF-I or agonist or analog thereof results in reduced incidence of Severe Intraventricular Hemorrhage (IVH) Grade III or IV through postmenstrual age (PMA) 36 weeks, 40 weeks, 6 months, 8 months, 10 months, or 12 months. In some embodiments, the administration of the IGF-I or agonist or analog thereof results in reduced incidence of retinopathy of prematurity (ROP) through postmenstrual age (PMA) 36 weeks, 40 weeks, 6 months, 8 months, 10 months, or 12 months.

The method disclosed herein comprises embodiments where the administration of the IGF-I or agonist or analog results in increased Functional Status as Assessed by PREMature Infant Index (PREMII) through postmenstrual age (PMA) 36 weeks, 40 weeks, 6 months, 8 months, 10 months, or 12 months.

For parenteral or oral administration, compositions of the complex may be semi-solid or liquid preparations, such as liquids, suspensions, and the like. Physiologically compatible carriers are those that are non-toxic to recipients at the dosages and concentrations employed and are compatible with other ingredients of the formulation. For example, the formulation preferably does not include oxidizing agents and other compounds that are known to be deleterious to polypeptides. Hence, physiologically compatible carriers include, but are not limited to, normal saline, serum albumin, 5% dextrose, plasma preparations, and other protein-containing solutions. Optionally, the carrier may also include detergents or surfactants.

In yet another aspect of the invention there is provided use of an IGF-I, an agonist or analog thereof in the manufacture of a therapeutic composition for treating a complication of preterm birth.

Finally, there is also provided an article of manufacture comprising packaging material and a pharmaceutical agent contained within the packaging material. The packaging material comprises a label which indicates that the pharmaceutical may be administered, for a sufficient term at an effective dose, for treating and/or preventing complications associated with preterm birth. The pharmaceutical agent comprises IGF-I, an agonist or an analog thereof together with a pharmaceutically acceptable carrier.

The invention will be further characterized by the following examples which are intended to be exemplary of the invention.

EXAMPLES

Example 1. Treatment of CLD in Extremely Premature Infants

An investigational drug comprising insulin like growth factor-1/insulin-like growth factor binding protein-3 (rhIGF-1/rhIGFBP-3) complex was studied for therapeutic effect in CLD. It is designed as a multicenter, randomized, open-label, controlled, 3-arm study to evaluate the clinical efficacy and safety of the therapeutic composition in preventing human chronic lung disease. This study is undertaken on subjects through 12 months corrected age (CA) compared to standard neonatal care in extremely premature infants. The study is reviewed and approved by the institutional review board (IRB)/independent ethics committee (IEC) of the responsible institution.

Purpose: The purpose of this study is to determine if an investigational drug comprising rhIGF-1/rhIGFBP-3 (henceforth, the therapeutic composition) can reduce respiratory complications in extremely premature babies through 12 months corrected age (CA), as compared to extremely premature babies receiving standard neonatal care alone.

Study Subjects: The subjects are between gestational age (GA) of 23 weeks+0 days and 27 weeks+6 days. Subjects include both sexes. At least fifty subjects are included in the study.

Exclusion criteria: The exclusion criteria include detectable gross malformation, known or suspected chromosomal abnormality, genetic disorder or syndrome, according to the investigator's opinion. The exclusion criteria also include persistent blood glucose level less than ($<$) 2.5 millimoles per liter (mmols/L) at the baseline visit to exclude severe congenital abnormalities of glucose metabolism; clinically significant neurological disease according to the investigator's opinion; monozygotic multiples; and any other condition that may pose risk to the subject or interfere with the subject's ability to be compliant with the protocol or interfere with the interpretation of results. If the subject is participating or plans to participate in a clinical study of another investigational study drug, device, or procedure (participation in observational studies is permitted on a case-by-case basis) are excluded. If the subject or subject's parent or legally authorized representative(s) is unable to comply with the protocol or is unlikely to be available for long-term follow-up as determined by the investigator, the subject is also excluded.

Details of the Study Design: The primary purpose of the study is prevention of Bronchopulmonary Dysplasia and Chronic Lung Disease. It is an open label study, and the intervention model will be Parallel Assignment. The conditions monitored will be BPD and CLD.

250 Micrograms/Kg/24 hours of the therapeutic composition is administered to one group of participants (Group A) by intravenous administration (IV) from birth up to postmenstrual age (PMA) 29 weeks+6 days. To another group of participants (Groups B), 400 micrograms/Kg/24 hours of the therapeutic composition is administered by intravenous administration (IV) from birth up to postmenstrual age (PMA) 29 weeks+6 days. To the third group (Group C or control group), standard neonatal care alone is provided.

The primary outcomes measured is incidence of Chronic Respiratory Morbidity (CRM) Through 12 Months Corrected Age (CA) [Time Frame: Baseline through 12 Months Corrected Age (CA)] CRM is a common adverse outcome of premature birth resulting in recurrent respiratory symptoms requiring treatment with pulmonary medications such as bronchodilators, need for supplementary home oxygen, frequent emergency room visits or hospital readmissions, especially during the first year of life. CRM will be measured by respiratory health care utilization and respiratory symptoms.

The secondary outcomes include incidence of Bronchopulmonary Dysplasia (BPD) at Postmenstrual Age (PMA) 36 Weeks [Time Frame: PMA Week 36]. BPD is a chronic lung disorder characterized by pulmonary immaturity, undifferentiated alveoli with the presence of hyaline membrane and atelectasis, dilated capillaries immersed in the mesenchyme, and a distorted deposition of the extracellular matrix. BPD results in residual effects on pulmonary function and is linked to neurodevelopmental problems during later childhood.

The secondary outcomes also include

Incidence of Severe Intraventricular Hemorrhage (IVH) Grade III or IV Through Postmenstrual Age (PMA) 40 Weeks [Time Frame: Baseline Through PMA 40 Weeks]

Incidence of Bronchopulmonary Dysplasia (BPD) at Postmenstrual Age (PMA) 40 Weeks [Time Frame: PMA Week 40]

Incidence of Chronic Respiratory Morbidity (CRM) or Death Through 6 Months Corrected Age (CA) [Time Frame: Baseline through 6 Months Corrected Age (CA)] CRM is a common adverse outcome of premature birth resulting in recurrent respiratory symptoms requiring treatment with pulmonary medications such as bronchodilators, need for supplementary home oxygen, frequent emergency room visits or hospital readmissions, especially during the first year of life. CRM will be measured by respiratory health care utilization and respiratory symptoms.

Functional Status as Assessed by PREMature Infant Index (PREMII) at Postmenstrual Age (PMA) 40 Weeks [Time Frame: PMA Week 36] PREMII is a Clinician-Reported Outcome (ClinRO) assessment used to capture overall functional maturation of extremely preterm neonates. Functional Status is defined as what the infant can do with respect to 8 key functional areas (feeding, weight gain, thermoregulation, respiratory support, apnea, bradycardia, desaturation events, and oxygen administration), as a reflection of the infant's overall health and development.

Example 2. BPD Prevention in Extremely Premature Infants

A randomized study for effect of IGF-1/IGFBP3 in BPD prevention was undertaken with an intervention model of parallel assignment. The study was conducted in multiple centers in Italy, the Netherlands. Poland, Sweden, the United Kingdom and the United States between 18 Jun. 2010 and 30 Mar. 2016.

The drug Mecasermin Rinfabate, that is IGF-1/IGFBP3, was administered as continuous intravenous infusion in subjects from Study Day 0 (day of birth) up to and including PMA 29 weeks+6 days, when the subject's endogenous production of IGF-1 is considered sufficient to maintain physiologic serum IGF-1 levels. After discontinuation of study drug infusion, each subject will be followed to PMA 40 weeks±4 days. The study was intended to determine the rhIGF-1/rhIGFBP-3 Dose. Administered as a Continuous Infusion (CI), required to establish and maintain longitudinal serum IGF-1 levels within physiological levels in premature infants, to prevent retinopathy of prematurity. This was a Phase 2, Randomized Controlled, Assessor-blind, dose confirming, pharmacokinetic, safety and efficacy of rhIGF-1/rhIGFBP-3. 61 Participants received insulin-like growth factor (rhIGF-I)/insulin-like growth factor binding protein-3 (rhIGFBP-3) 250 microgram per kilogram (mcg/kg) for 24 hours through continuous intravenous (IV) infusion from Day 0 up to 29 weeks 6 days of post-menstrual age (PMA). As a control group, 60 participants received standard of care alone. Table 1 illustrates the participant flow of the overall study

TABLE 1

| Participant Flow: Overall Study | | |
|---|---|---|
| | rhIGF-1/ rhIGFBP-3 | Standard of Care (Control) |
| STARTED | 61 | 60 |
| COMPLETED | 46 | 46 |
| NOT COMPLETED | 15 | 14 |
| Withdrawal by Subject | 2 | 1 |
| Adverse Event | 11 | 9 |
| Protocol Deviation | 2 | 2 |
| Administrative Decision | 0 | 1 |
| Other Unspecified | 0 | 1 |

TABLE 2

| illustrates the population in the study. | | | | | | |
|---|---|---|---|---|---|---|
| | rhIGF-1/ rhIGFBP-3 | | Standard of Care (Control) | | Total | |
| Overall Participants Analyzed [Units: Participants] | 61 | | 60 | | 121 | |
| Age [Units: Weeks] Mean (Standard Deviation) | 25.60 (1.207) | | 25.62 (1.397) | | 25.61 (1.300) | |
| Sex: Female, Male [Units: Participants] Count of Participants | | | | | | |
| Female | 22 | 36.1% | 21 | 35.0% | 43 | 35.5% |
| Male | 39 | 63.9% | 39 | 65.0% | 78 | 64.5% |

The secondary outcomes in a continuation of the study included among other parameters:

Time to Discharge From Neonatal Intensive Care (TD-NIC) [Time Frame: Day 0 to 40 Weeks Post Menstrual Age (EOS)]

Number of Participants With Bronchopulmonary Dysplasia (BPD) [Time Frame: At 36 Weeks Post Menstrual Age]

Severity of BPD as mild, moderate and severe were based on the National Institute of Child Health and Human Development (NICHD) guidelines for preterm infants born at gestational age (GA) less than (<) 32 weeks.

Mild: oxygen requirement during the first 28 days but in room air at PMA 36 weeks or discharge to home, whichever comes first.

Moderate BPD: oxygen requirement during the first 28 days and oxygen <30 percent (%) at PMA 36 weeks or discharge to home, whichever comes first.

Severe BPD: oxygen requirement during the first 28 days and oxygen greater than equal ($\geq$)30% through head hood or nasal canula, or continuous positive airway pressure, or mechanical ventilation, or high flow nasal cannula $\geq$2 L/min at PMA 36 weeks or discharge to home, whichever comes first.

Rate of Change in Body Weight [Time Frame: Day 0 to 40 Weeks Post Menstrual Age (EOS)] The rate of change is the rate of specific body weight change per day in kilogram (kg).

Rate of Change in Length [Time Frame: Day 0 to 40 Weeks Post Menstrual Age (EOS)]

The rate of change is the length change per day in centimeter (cm). Number of Participants With Treatment Emergent Adverse Event (TEAE) and Treatment Emergent Serious Adverse Event (TESAE) [Time Frame: Day 0 to 40 Weeks Post Menstrual Age (EOS)]

An adverse event (AE) was any untoward medical occurrence in a participant who received study drug without regard to possibility of causal relationship. A serious adverse event (SAE) was an AE resulting in any of the following outcomes or deemed significant for any other reason: death; initial or prolonged in-patient hospitalization; life-threatening experience (immediate risk of dying); persistent or significant disability/incapacity; congenital anomaly.

Treatment-emergent adverse event was defined as the onset of any AE or if the severity of a pre-existing AE worsened any time on or after the date of first dose of investigational product.

Percentage of Serum IGF-1 Concentrations Falling Within Target Range After Infusion of rhIGF-1/rhIGFBP-3 [Time Frame: Day 0 to 40 Weeks Post Menstrual Age (EOS)]

Serum samples were collected from treated and control participants for quantitation of IGF-1 using validated immunoassays. Target range of serum IGF-1 was 28-109 mcg/L. The percentage of serum IGF-1 levels across treated participants that fall within the range was reported.

Serum Concentrations of IGFBP-3 After Intravenous (IV) Infusion of rhIGF-1/rhIGFBP-3 [Time Frame: Day 0 and Week 40 Post Menstrual Age]

Serum Concentrations of Acid Labile Sub-unit (ALS) After Intravenous (IV) Infusion of rhIGF-1/rhIGFBP-3 [Time Frame: Day 7 and Week 40 Post Menstrual Age]

TABLE 3 illustrates the measured values of BPD as secondary outcome.

| | rhIGF-1/ rhIGFBP-3 | Standard of Care (Control) |
|---|---|---|
| Participants Analyzed [Units: Participants] Number of Participants With Bronchopulmonary Dysplasia (BPD) [Units: Participants] | 47 | 49 |
| No BPD | 4 | 4 |
| Mild | 23 | 16 |
| Moderate | 9 | 5 |
| Severe | 10 | 22 |
| Unable to determine | 1 | 2 |

No statistical analysis provided for Number of Participants With Bronchopulmonary Dysplasia (BPD).

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists. (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A method of treating Chronic Lung Disease comprising administering to a premature infant a composition comprising an equimolar complex of insulin-like growth factor-I (IGF-1) and insulin-like growth factor binding protein-3 (IGFBP-3), wherein the complex is administered by continuous intravenous infusion at a dosage of complex of about 400 micrograms/kg/24 hours from birth to post-menstrual age of about 24 to 34 weeks.

2. The method of claim 1, wherein the infant was prematurely born by at least 1 week, 2 weeks, 3 weeks, 4 weeks, 1 month, 2 months, or 3 months.

3. The method of claim 1, wherein the complex is administered from the time of birth up to PMA of about 28 to 32 weeks.

4. The method of claim 1, wherein the complex is administered from the time of birth up to PMA of about 29 weeks plus 6 days.

5. The method of claim 1, wherein the IGF-1, or IGFBP-3 or both are recombinantly produced.

6. The method of claim 1, wherein Chronic Lung Disease is Bronchopulmonary dysplasia (BPD).

\* \* \* \* \*